US011260247B2

(12) United States Patent
Coviello et al.

(10) Patent No.: US 11,260,247 B2
(45) Date of Patent: Mar. 1, 2022

(54) PASSIVE ULTRASOUND IMAGING WITH SPARSE TRANSDUCER ARRAYS

(71) Applicant: Isis Innovation Limited, Summertown (GB)

(72) Inventors: Christian Coviello, Oxford (GB); Richard Kozick, Lewisburg, PA (US); Constantin Coussios, Oxford (GB)

(73) Assignee: OXSONICS LIMITED, Oxford (GB)

( * ) Notice: Subject to any disclaimer, the term of this patent is extended or adjusted under 35 U.S.C. 154(b) by 841 days.

(21) Appl. No.: 14/427,667

(22) PCT Filed: Sep. 13, 2013

(86) PCT No.: PCT/GB2013/052410
§ 371 (c)(1),
(2) Date: Mar. 12, 2015

(87) PCT Pub. No.: WO2014/041370
PCT Pub. Date: Mar. 20, 2014

(65) Prior Publication Data
US 2015/0224346 A1    Aug. 13, 2015

(30) Foreign Application Priority Data
Sep. 14, 2012    (GB) ..................................... 1216455

(51) Int. Cl.
*G01S 7/52* (2006.01)
*G01S 15/89* (2006.01)
(Continued)

(52) U.S. Cl.
CPC .............. *A61N 7/00* (2013.01); *A61B 8/4494* (2013.01); *A61B 8/5207* (2013.01);
(Continued)

(58) Field of Classification Search
CPC ....... A61B 8/5207; A61B 8/4494; A61B 8/00; A61B 8/08; A61B 8/44; A61B 8/4444;
(Continued)

(56) References Cited

U.S. PATENT DOCUMENTS

| 5,537,367 A | 7/1996 | Lockwood et al. |
| 2003/0220554 A1 | 11/2003 | Grenon et al. |
| 2005/0143655 A1* | 6/2005 | Satoh .................. G01S 7/52047 600/443 |

FOREIGN PATENT DOCUMENTS

WO    WO 2010/031057 A1    3/2010

OTHER PUBLICATIONS

Hoctor, R.T. et al., "The Unifying Role of the Coarray in Aperture Synthesis for Coherent and Incoherent Imaging", Proceedings of the IEEE, New York, vol. 78, No. 4, pp. 735-752, Apr. 1990.
(Continued)

*Primary Examiner* — Carolyn A Pehlke
(74) *Attorney, Agent, or Firm* — Wegman Hessler

(57) ABSTRACT

A passive compression wave imaging system comprises an array of sensor elements arranged in a sparse array and a processor arranged to: store a plurality of samples of the output from each of the sensor elements over a sample period; derive from the stored samples a value for each of a set of image pixels; wherein for each of the image pixels the processing means is arranged to: define a plurality of different sets of weights for the elements of the sparse array; calculate a component of a pixel value from each of the sets of weights and the stored samples; and sum the components of the pixel value to produce a final pixel value.

18 Claims, 8 Drawing Sheets

1. Form Difference Coarray

El 13
El 5

2. Sample Coarray Weighting Function
Value of C sampled at $C_d$

C
$C_d$

3. Place Into Weight Matrix

Element$_j$
13
Element$_i$
5
$C_w$

(51) Int. Cl.
*A61B 8/00* (2006.01)
*A61N 7/00* (2006.01)
*A61B 8/08* (2006.01)
*G10K 11/34* (2006.01)

(52) U.S. Cl.
CPC ...... *G01S 7/52047* (2013.01); *G01S 15/8925* (2013.01); *A61N 2007/0052* (2013.01); *G10K 11/34* (2013.01)

(58) Field of Classification Search
CPC ....... A61B 8/4483; A61B 8/4488; A61B 8/48; A61B 8/481; A61B 8/52; G01S 7/52047; G01S 7/52; G01S 15/8925; G01S 7/52085; G01S 7/52095; G01S 15/8915; G01S 15/8927; G10K 11/34; G10K 11/346; A61N 2007/0004; A61N 2007/0039; A61N 2007/0052; A61N 7/00; A61N 7/02
USPC ......................................................... 600/439
See application file for complete search history.

(56) References Cited

OTHER PUBLICATIONS

Kozick, R.J. et al., "Application of the Singular Value Decomposition to Aperture Synthesis with Boundary Arrays", Proceedings of the Antennas and Propagation Society Annual Meeting 1991, IEEE, pp. 526-529, Jun. 24, 1991.

Kozick, R. J. et al., "Linear Imaging with Sensor Arrays on Convex Polygonal Boundaries", IEEE Transactions on Systems, Man and Cybernetics, IEEE Inc., vol. 21, No. 5, pp. 1155-1166, Oct. 1991.

Coviello, C. et al., "Robust Capon Beamforming for Passive Cavitation Mapping during HIFU Therapy", 160th Meeting of Acoustical Society of America, Abstract published in Journal of the Acoustic Society of America, 2010.

Collin, J., et al., "Integration of an Acoustically Transparent Passive Cavitation Detection Array with a Clinical High Intensity Focused Ultrasound Device", 11th International Symposium Therapeutic Ultrasound, New York, 2011.

Faragher, S., "Cavitational Methods for Characterising and Testing Clinical High-Intensity Focused Ultrasound Systems", Ph.D. Dissertation, Department of Engineering Science, University of Oxford, Oxford UK, 2011.

Gyongy, M., "Passive Cavitation Mapping for Monitoring Ultrasound Therapy", Ph.D. Dissertation, University of Oxford, Oxford UK, 2011.

Gyongy, M. et al., "Passive Cavitation Mapping with Temporal Sparsity Constraint", Journal of the Acoustic Society America, vol. 130, No. 5, pp. 3489-3497, 2011.

Coviello, C.M. et al., "Thin-Film Sparse Boundary Array Design for Passive Acoustic Mapping During Ultrasound Therapy", IEEE Transactions on Ultrasonics, Ferroelectrics, and Frequency Control, IEEE, vol. 59, No. 10, pp. 2322-2330, Oct. 2012.

Search Report under Section 17 dated Jan. 8, 2013 for GB 1216455.4 filed Sep. 14, 2012.

International Search Report and Written Opinion dated Dec. 2, 2013 for PCT/GB2013/052410 filed Sep. 13, 2013.

International Preliminary Report on Patentability dated Mar. 17, 2015 for PCT/GB2013/052410 filed Sep. 13, 2013.

Vasant, A. et al., "Passive Cavitation Imaging with Ultrasound Arrays", Journal of the Acoustical Society of America, vol. 126, No. 6, pp. 3071-3083, Dec. 2009.

Coviello, C., "Robust Capon Beamforming for Passive Cavitation Mapping during HIFU Therapy", 160th Meeting of Acoustical Society of America, Abstract published in Journal of the Acoustic Society of America, 2010.

Jensen, C. et al., "Spatio-Temporal Monitoring of HIFU Therapy by Passive Acoustic Mapping" Radiology, vol. 262, No. 1, pp. 252-261, 2012.

Ralph T. Hoctor, et al.; "The Unifying Role of the Coarray in Aperture Synthesis for Coherent and Incoherent Imaging."; Proceedings of the IEE, Apr. 1990, pp. 735-752, vol. 78, No. 4.

* cited by examiner

PASSIVE ULTRASOUND IMAGING WITH SPARSE TRANSDUCER ARRAYS

CROSS-REFERENCE TO RELATED APPLICATIONS

This application claims the priority filing benefit of International PCT Application PCT/GB2013/052410 filed Sep. 13, 2013 and published under PCT 21(2) in the English language, Great Britain Patent Application Serial No. 1216455.4 filed Sep. 14, 2012. Each of the above listed applications is incorporated herein by reference.

FIELD OF THE INVENTION

The invention relates to passive ultrasound imaging, and in particular to the use of sparse transducer arrays for passive ultrasound imaging. It has various applications including the real time mapping of sources of broadband emissions (such as ineritially cavitating bubbles) or sources of harmonic emissions, and other effects during therapeutic ultrasound treatment.

BACKGROUND TO THE INVENTION

Real-time treatment monitoring of therapeutic ultrasound, i.e., the determination of both the spatial extent and dose of the therapy, is a key issue for widespread clinical adoption, whether the application is high-intensity focused ultrasound (HIFU) ablation of cancerous tissue or ultrasound-enhanced targeted drug delivery.

In fact, one of the key limitations of HIFU surgery is the lack of an affordable and effective real-time monitoring strategy. Several different affordable ultrasound (US)-based monitoring methods have been suggested, including interleaving B-mode imaging and therapy pulses and harmonic motion detection. Neither of these methods specifically monitors acoustic cavitation, which has been shown to enhance both HIFU surgery and drug delivery. Also, neither of these methods can specifically monitor harmonic emissions emanating from the therapeutic focus in the absence of an ultrasound contrast agent.

Further, interleaving B-mode and HIFU is not truly real time, and harmonic motion detection applies only to thermal-based therapies. Instead, recent work has shown that passive spatial mapping of the acoustic emissions using diagnostic linear-array probes has tremendous promise both for focus localization and real-time treatment monitoring and the method applies to both HIFU surgery and drug delivery (C. Jensen, R. Ritchie, M. Gyongy, J. R. T. Collin, T. Leslie and C.-C. Coussios, "*Spatio-Temporal Monitoring of HIFU Therapy by Passive Acoustic Mapping*", Radiology 262(1): 252-261 (2012).

However, linear arrays are only able to map emissions in one plane, whereas a 2-D array can provide full 3-D spatial coverage, providing more information regarding the extent of treatment. When designing 2-D sensor arrays for passive imaging, two key characteristics are the aperture size and the layout geometry, because these dictate the resolution of the targeted activity. Thus, to be able to image in the transverse, elevation, and axial directions with suitable resolution requires a large 2-D aperture. The financial cost and complexity, however, associated with large, fully-filled and regularly-spaced 2-D arrays increases dramatically with the size of the aperture to be used. This is especially true when the added per-channel cost of amplification, filtering, and digitization of each array element is considered. Further, the cost of manufacturing an array from traditional piezoceramics can be expensive and time-consuming because of the manufacturing process.

There is therefore a need for a 2-D monitoring array that overcomes the shortcomings of traditional ultrasound array design to achieve passive acoustic mapping using an array with a small number of elements.

SUMMARY OF THE INVENTION

The present invention providesa passive compression wave imaging system comprising an array of sensor elements arranged in an array, which may be a sparse array, and processing means arranged to: store a plurality of samples of the output from each of the sensor elements over a sample period; and derive from the stored samples a value for each of a set of image pixels. For each of the image pixels the processing means may be arranged to perform one or more of the following steps:
 a. define a plurality of different sets of weights for the elements of the sparse array;
 b. calculate a component of a pixel value from each of the sets of weights and the stored samples; and
 c. sum the components of the pixel value to produce a final pixel value.

The compression waves may be ultrasound waves. The processor may be arranged to calculate the sets of weights for the array and store them. The processor may then be arranged to use the stored values of the weights to generate a plurality of images from a plurality of sets of stored samples. Alternatively the processor may be arranged to calculate the sets of weights for each image.

For each of the image pixels, the processing means may be arranged to calculate for each of the sensor elements, a delay corresponding to the time the compression waves will take to travel from the point imaged by the pixel to the sensor element.

The processing means may be arranged, for each of the image pixels, to shift the stored data from at least one of the sensor elements on the basis of the delays. This may be arranged to align the data temporally, so that sensor data for the same event in the imaged area is aligned.

For each pixel of the image, the weights may be related to each other in a manner defined by a weight mask. The weight mask may define a set of weights for a set of points. The weights of the weight mask may be related to each other by a weight mask function. The weight mask function may be a continuous function. The function, or the weight mask, may be centred at a different point in the array coarray, or a different point in the array, for each pixel. Each time a set of weights is calculated to form an image, the calculation may include calculating the weight mask values form the weight mask function, or it may be based on values of the weight mask stored in memory.

The weight mask function may have a main area that corresponds to an area of the coarray, and a boundary area covering parts of the coarray not covered by the main area, the boundary area being of a single constant value.

The processing means may be arranged, in determining each set of weights, to determine from the coarray weight mask an element space matrix having matrix elements corresponding to pairs of the array elements.

The processing means may be arranged to derive, from the element space matrix, at least one pair of weight vectors each having a weight for each of the array elements, and to derive from the pair of weight vectors a value for the pixel of the image.

The processing means may be arranged to derive, from the element space matrix, a plurality of pairs of weight vectors. The processing means may be arranged to select from said plurality of pairs of weight vectors, a group of the most significant pairs, and to derive a pixel value only from each of said group.

The present invention further provides a method of passive compression wave imaging comprising: providing an array of sensor elements arranged in a sparse array; storing a plurality of samples of the output from each of the sensor elements over a sample period; deriving from the stored samples a value for each of a set of image pixels; wherein for each of the image pixels the method includes any one or more of: defining a plurality of different sets of weights for the elements of the sparse array; calculating a component of a pixel value from each of the sets of weights and the stored samples; and summing the components of the pixel value to produce a final pixel value.

The step of defining a plurality of sets of weights, may be performed each time an image is produced, or may be performed and the weights stored in memory. The step of calculating the components of the pixel values may therefore be performed using stored values of the weights or values calculated for the image being formed.

For each of the image pixels, the method may include calculating for each of the sensor elements, a delay corresponding to the time the compression waves will take to travel from the point imaged by the pixel to the sensor element.

The method may include, for each of the image pixels, shifting the stored data from at least one of the sensor elements on the basis of the delays.

The method may include, for each pixel of the image, deriving the weights using a weight mask function, and shifting the weight mask function, or a weight mask, for each pixel.

The method may include defining a coarray of the sensor array. The coarray may define a plurality of points. These may include some points corresponding to the sensor array element positions. The weight mask function may have a main area that corresponds to the area of a coarray. The method may include identifying elements of the coarray not covered by the main area of the weight mask function and allocating a single constant value to those points.

Determining each set of weights may include determining from the coarray weight mask an element space matrix having matrix elements corresponding to pairs of the array elements.

The method may include deriving, from the element space matrix, at least one pair of weight vectors each having a weight for each of the array elements, and deriving from the pair of weight vectors a value for the pixel of the image.

The method may include deriving from the element space matrix, a plurality of pairs of weight vectors. The method may include selecting from said plurality of pairs of weight vectors, a group of the most significant pairs, and deriving a pixel value only from each of said group.

In some embodiments of the invention, we use the concept of the coarray (described in R. Hoctor and S. Kassam, "The unifying role of the coarray in aperture synthesis for coherent and the unifying role of the coarray in aperture synthesis for coherent and incoherent imaging," *Proc. IEEE*, vol. 78, no. 4, pp. 735-752, April 1990, and also in R. Kozick and S. Kassam, "Linear imaging with sensor arrays on convex polygonal boundaries," *IEEE Trans. Syst. Man Cybern.*, vol. 21, no. 5, pp. 1155-1166, September/October 1991.) to synthesize a fully-filled 2-D weighted aperture.

This provides the performance of an array with much higher element count but with much reduced complexity and cost at the expense of additional signal processing. Other examples of arrays for passive acoustic mapping of broadband emissions related to ultrasound therapy have been reported (for example in J. Collin, R. Ritchie, M. Gyongy, D. Cranston, F. Wu, T. Leslie, and C.-C. Coussios, "Integration of an acoustically transparent passive cavitation detection array with a clinical high intensity focused ultrasound device," in 11th Int. Symp. Therapeutic Ultrasound, New York, N.Y., and S. Faragher, "Cavitational methods for characterising and testing clinical high-intensity focused ultrasound systems," Ph.D. dissertation, Department of Engineering Science, University of Oxford, Oxford, UK, 2011.) but these studies used random arrays or did not exploit the coarray to improve performance.

Random arrays (with sensor positions chosen according to a probability distribution) are one approach to producing a large aperture with few sensor elements. The point spread function (PSF) of a random array is itself a random function, but on average, the PSF is characterized by a main lobe with a fairly uniform side lobe level. Arrays that are deterministically thinned by omitting elements at locations along a regular grid typically have PSFs with large side lobes in certain directions (grating lobes). Some embodiments of this invention use a particular thinned 2-D array with elements on the boundary of a rectangle, and signal processing to achieve imaging performance that is comparable to a filled rectangular array. The key property is that the boundary and filled arrays share the same coarray, so the boundary array is capable of producing the same images through additional data collection and signal processing.

Recordings of acoustic emissions from therapeutic ultrasound show both harmonic and broadband components, implying the possible presence of both stable and inertial cavitation, as well as scattering of nonlinear components of the incident wave by tissue. Diagnostic ultrasound probes in previous passive acoustic mapping studies are made from traditional piezoceramic materials. Because of the relatively narrowband behavior of the piezomaterials used, these probes are typically designed with a relatively small bandwidth because the goal is to optimize active imaging at a particular frequency. This can mean that much of the broadband component of the acoustic emissions is lost. Although recent temporal sparse reconstruction techniques that attempt to recover out-of-band frequencies to improve the quality of acoustic maps have shown promise, (for example M. Gyongy and C. Coviello, "Passive cavitation mapping with temporal sparsity constraint," *J Acoust. Soc. Am.*, vol. 130, no. 5, pp. 3489-3497, 2011), a further advantage of using thin film technology is the opportunity for wideband detection and high sensitivity on receive. Thin-film materials such as polyvinylidene fluoride (PVDF) and PVDF copolymers such as P(VDF-TrFE) have long been used in a variety of ultrasound sensors for exactly these reasons, and are particularly suitable for the present invention because of the advantageous acoustic sensing properties as well as the low cost of construction and easily configurable array design.

The system may further comprise, in any combination, any one or more features of the preferred embodiments of the invention which will now be described by way of example only with reference to the accompanying drawings.

BRIEF DESCRIPTION OF THE DRAWINGS

FIG. 6 is a graph of frequency content of the signal received at the array of the system of FIG. 5a;

DESCRIPTION OF EMBODIMENTS OF THE INVENTION

Figure 1B:
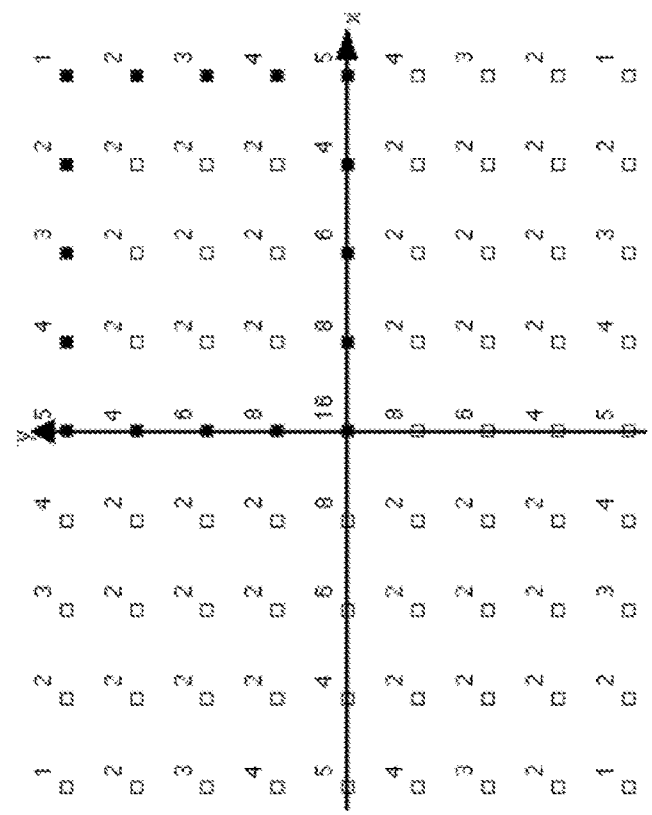
FIG. 1 is a diagram of a sparse sensor array forming part of an embodiment of the invention, and its associated coarray.

As one example of the application of the present invention is in mapping of cavitation during ultrasound therapies, a basic method of mapping such cavitation will first be described. Ultrasound therapies are emerging as competitive options in the treatment of various cancer types because of their ability to tightly focus energy deep into the body completely noninvasively with few adverse side effects. One of several key phenomena that can be exploited and monitored during ultrasound therapy is that of acoustic cavitation, or the nucleation and oscillation of microscopic bubbles caused by acoustic waves travelling in the body. Cavitation has the potential to enhance the local heating rate during HIFU ablation and can also augment desired mechanical bioeffects of ultrasound. This is useful in applications such as the dissolution of blood clots (thrombolysis), tissue homogenization (histotripsy), and aiding in cell permeability for drug transport. Of the two general regimes of cavitation, inertial cavitation, which is the rapid expansion and collapse of a bubble, is of primary concern in the context of monitoring therapy. The bubble collapse, being an impulse-like event in the time domain, generates broadband acoustic emissions which, in addition to their helpful bioeffects, can also be used to monitor the spatial extent of the therapy.

Assume that we have a sensor array located at positions defined in a coordinate system by $x_j=(x_j, y_j, z_j)^T$ for $j=1, 2, \ldots, 4(N-1)$ sensors. Let $A=\{x_j : j=1, 2, \ldots, 4(N-1)\}$ be the set of sensor array element locations. The source strength measured by the array of sensors at a position x is given as $$q(x, t) = \frac{4\pi}{4(N-1)\alpha} \sum_{j=1}^{4(N-1)} d_j(x) s_j(t - d_j(x)/c) \quad (1)$$

where $s_j(t)$ is the signal recorded on channel j, $\alpha$ is a conversion factor from pressure to voltage, and the distance from sensor element to source field position is $$d_j(x) = \sqrt{(x_j-x)^2+(y_j-y)^2+(z_j-z)^2} \quad (2)$$

The source power $\Psi(x)$ can then be found by time-averaging the source strength $q(x,t)$ $$\Psi(x) = \frac{1}{4\pi\rho_0 cT} \int_{t_0}^{t_0+T} |q(x, t)|^2 \, dt \quad (3)$$

where $\rho_o$ is the density of the medium and c is the speed of propagation. Although in conventional passive acoustic mapping, apodization or weighting functions are not applied to the power estimates, it is known to apply weights to shape the receive beam to reduce the effect of noise and unwanted reflections. Weighting based on optimal beamforming criteria has also been demonstrated previously (for example C. Coviello, "Robust Capon beamforming for passive cavitation mapping during HIFU therapy," in 160th Meeting of Acoustical Society of America, Abstract published in J. Acoust. Soc. Am. (2010).

In an embodiment of the invention a square array of detector elements are each arranged to output a signal that varies with the intensity of ultrasound signal that is incident upon them, over a broadband frequency range. The signals are input to a processor which is arranged to sample each of the signals or channels repeatedly at a sampling frequency, and the values for each channel are stored as a one-dimensional array, or vector. The processor is then arranged to perform a number of steps to generate an image data set comprising a value for each pixel of the image.

Then, to form an image of an imaged area, a value for each pixel of the image has to be derived from the stored channel vectors. For each pixel, a delay is calculated for each element in the sensor array, which is the time taken for the ultrasound to travel form the point being imaged in the pixel to the element of the sensor array. The data in each of the channels is then shifted by an amount dependent on the respective delay, so as to temporally align the channels. The data from each of the channels is then weighted, using a weighting algorithm. The weighting algorithm defines a plurality of sets of sub-image weightings for the square array elements. These weightings are then applied to the stored channel vectors, and the data combined to obtain a sub-image value for the pixel as will be described in more detail below. Several sub-image values are derived for each pixel, using the different weightings for the data, and summed linearly to derive a total value for the pixel. This process is repeated for each pixel in the image, in each case re-calculating the delays and using different weightings specific to that pixel, thereby generating a complete image data set that can then be used to generate an image.

In one embodiment of the invention, in order to simulate an image formed from a filled square array, two components of the source strength, or pixel value, in (1) are computed using the sampled values of the signals from the sensor array, with different weights $w_{1,j}$ and $w_{2,j}$ applied to each array element:

$$q(x, t) = \beta \sum_{j=1}^{4(N-1)} w_{kj} d_j(x) s_j(t + d_j(x)/c) \quad (4)$$

for k=1, 2, and where $\beta=(4\pi)/(4(N-1)\alpha)$. Strictly speaking, in near-field imaging, the weight vector, $w_{k,j}$, will have a range dependence, although this is omitted from (4). The source power estimate $\Psi(x)$, then, in (3) is generalized with weighting as $$\Psi_w(x) = \frac{1}{4\pi\rho_0 cT} \int_{t_0}^{t_0+T} q_1(x,t) q_2(x,t)^* \, dt \qquad (5)$$

where * denotes the complex conjugate.

Utilizing the concept of the coarray, weights may be chosen over a sparse array that allow higher quality passive imaging compared with a sparse array and conventional passive acoustic mapping. The concept of the coarray and an example of how the weights can be calculated will be described below.

Figure 1A:
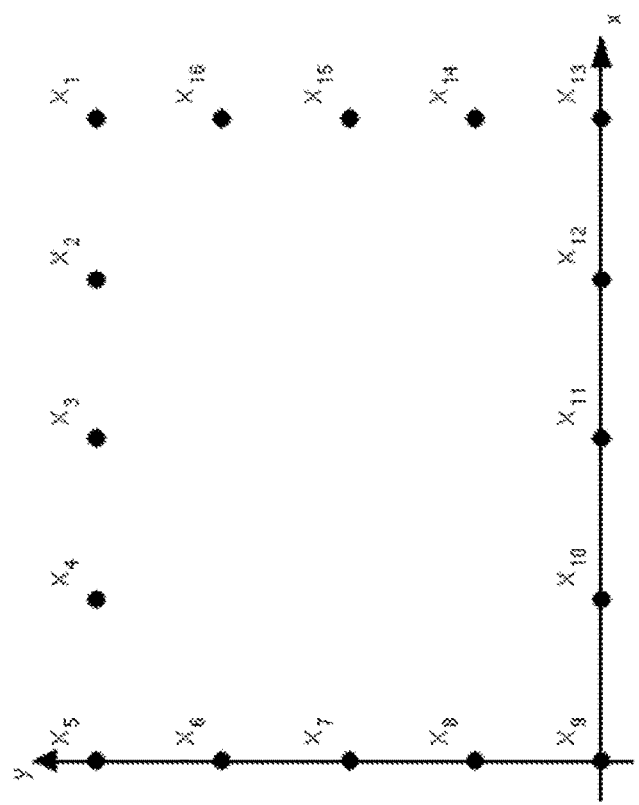

Referring to FIG. 1a, a rectangular boundary array comprises four rows of sensors, each row defining, or being arranged along, one side of the rectangle. In this embodiment the rectangle is a square, with the number N of elements per side being equal, in this case 5, so the array has a total of 4(N−1)=16 elements. The positions of the elements are defined by position vectors $x_i$ in a coordinate system where i is the index over the elements of the array. It should be noted that the pixel array positions correspond to the sensor element array positions and both are defined in the same coordinate system. For any array, the coarray, specifically the difference coarray $C_d$ when describing passive imaging, is defined as the "set of all vector differences between points in the aperture".

$$C_d = \{y | y = x_i - x_j, \forall x_i, x_j \in A\} \qquad (6)$$

where j is a separate index over elements of the array.

The difference coarray for the N=5 boundary array is shown in FIG. 1b, with the multiplicity of each point in the coarray shown. Each point in the coarray is associated with a position vector, and the coarray is defined in the same coordinate system as the sensor array. The multiplicity of each point of the coarray is the number of pairs of points on the array that are separated by the vector corresponding to that point on the coarray. The coarray is also the support of the inverse Fourier transform of the PSF and the morphological autocorrelation of the array. If array weights $w_{1,j}$ and $w_{2,j}$ are used as in (4) and (5), then the inverse transform of the resulting PSF can be written as the cross-correlation of the weights applied to the detector elements $$\gamma(y) = \sum_{\{i,j:\, y=x_i-x_j\}} w_{1,i} w_{2,j}^*, \; y \in C_d \qquad (7)$$

which is called the coarray weight mask.

The fundamental point to consider is that the difference coarray of a fully-filled rectangular array and that of a sparse rectangular boundary array are equivalent, meaning that the sparse array should be able to achieve imaging performance comparable to the fully-filled array. However, it is necessary to determine the weighting to be applied to the array, specifically to each element on the array, so as to limit the effect of side lobes. A boundary array having fewer elements than a fully-filled array has a more limited number of combinations of individual weightings that could be applied in a fully-filled array. Linear imaging, i.e. the linear addition of a number of intermediate or sub-images, can however be used to allow multiple sets of weights to be applied to the sparse array elements, to enable the construction of multiple intermediate images which are then coherently combined to yield the final image. This provides variability in weighting combinations equivalent to that with a fully filled array.

Figure 2:
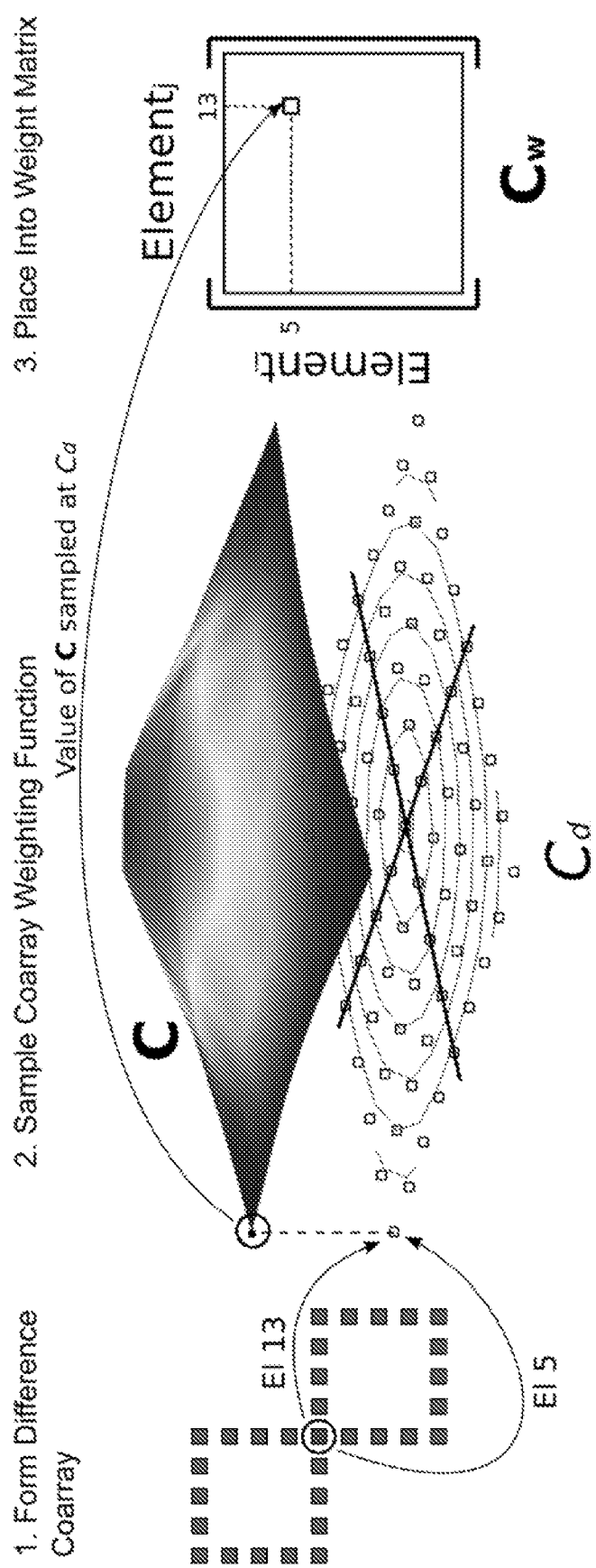
FIG. 2 is a diagram showing some steps of a method of processing sensor signals in an embodiment of the invention.

Referring to FIG. 2, given a desired weighting function defined for a fully filled array, to replicate this with a sparse array it is necessary to synthesize the individual sub-image weights to be applied, using a weight synthesis algorithm. First, a 2-D weighting mask, γ(y), is chosen over the coarray $C_d$, which is represented by a matrix C of size (2N−1)×(2N−1). Since the coarray elements include the sparse array elements the matrix has a weighting for each element of the sparse array, as well as the 'additional' elements of the coarray that are not part of the sparse array. This matrix C needs to be centred on the pixel for which the value is to be calculated, and is therefore shifted, in the coordinate system of the coarray, after the calculations are performed for one pixel, so as to be correctly aligned for the calculations for the next pixel. For the central pixel of the coarray the matrix is aligned with the coarray. For other pixels, the matrix C is shifted so that it is centred on the pixel to be calculated. For elements of the coarray that are not covered by the shifted matrix, a value is assigned, which in this case is the lowest value in the original matrix. The weight mask can be, for example a 2D sinc function, a 2D Chebyshev function, or a 2D Blackman function. The appropriate choice of weight function is driven by the expected dimensions of the region with active acoustic sources.

The goal of the weight synthesis algorithm is to decompose C into a sum of matrices, each of which is an outer product of two weight vectors, each of size 4(N−1)×1, with outer product being used to make an intermediate image. To do so, we need a mapping from the coarray weighting mask represented by C, to a 4(N−1)×4(N−1) matrix $C_w$ of element-pair weights, shown in FIG. 2. $C_w$ is a square matrix, with each row being associated with one of the sparse array elements, and each column being associated with one of the sparse array elements. Therefore each point in the matrix is associated with a pair of array elements. Because $C_d$ is a difference coarray as described above, each element in $C_d$ is formed from, i.e. is associated with, one or more different pairs of array elements, and the array weighting mask represented by C is sampled over $C_d$. Thus, by taking the value of C at each point in $C_d$ normalized by (divided by) the multiplicity and mapping it to the point of $C_w$ on the row and column associated with the pair of elements, or each pair of elements, that contributed to it (or is associate with it), we get the mapping from difference co-array to array element space.

Now, with $C_w$ in hand, we then decompose it using the singular value decomposition (SVD) so as to derive a pair of 4(N−1)×1 weight vectors, each having one weight for each of the sparse array elements, for each sub-image value for the pixel $$C_w = USV^H = \sum_{\ell=1}^{4(N-1)} u_\ell \sigma_\ell v_\ell^H \qquad (8)$$

Where:
H denotes conjugate-transpose;
$u_i$ are the left singular vectors
$\sigma_i$ are the singular values
$v_i$ are the right singular vectors.

Let l be the index over sub-images, and w1(l), w2(l) be the two 4(N−1)×1 weight vectors used to form $q_1(x,t; l)$ and $q_2(x,t; l)$ using (4). Then assign $w_1(l) = u_l \rho_l^{1/2}$ and $w_2(l)$ $=v_l\rho_l^{1/2}$ for $l=1, \ldots, 4(N-1)$, so we have the weight vector pairs for each sub-image, and the sub-image value for the pixel is computed using (5):

$$\Psi_\ell(x) = \frac{1}{4\pi\rho_0 cT} \int_{t_0}^{t_0+T} q_1(x, t; \ell) q_2(x, t; \ell)^* \, dt \quad (9)$$

Finally, all of the sub-images are summed together to form the output image:

$$\Psi_{TOTAL}(x) = \sum_\ell \Psi_\ell(x) \quad (10)$$

The complete algorithm description is shown in Algorithm 1 (see Appendix 1).

A variable of this process is how many intermediate images to use, with the maximum being $4(N-1)$. In practice, for each pixel of the final image, only a few singular values are significant, so the image addition in (10) may be truncated with negligible effect on image quality.

For efficiency, rather than computing the weights for each image pixel as described above, the weights can be pre-computed for all ranges once the sensor array is fixed. For a rectangular boundary array, this would require storage of a $(N \times N \times 2)$ matrix of weights per pixel position. Depending on the processing system to be used, this gives a trade-off of memory size and access versus computation speed. It can also be noted that Algorithm 1 is very parallelizable for potential implementation on graphical processing units (GPUs) or other multiprocessor systems.

A means of assessing the potential performance of an imaging array is that of the point spread function (PSF), which allows the determination of the possible imaging resolution. For a 2-D sparse array and a point source at position $x_s = (x_s, y_s, z_s)T$, let us start by assuming that the array is situated in the XY-plane ($z_j = 0, \forall j$); then, the PSF as a function of frequency f and position x can be written as $$P(x, f) = \left| \sum_{j=1}^{4(N-1)} w_j \exp\{j\phi(x_j)\} \right|^2 \quad (11)$$

$$\phi(x_j) = \quad (12)$$
$$k \left( \sqrt{(x-x_j)^2 + (y-y_j)^2 + z^2} - \sqrt{(x_s-x_j)^2 + (y_s-y_j)^2 + z_s^2} \right)$$

where $w_j$ is the weighting on array element j, and $k=(2\pi f)/c$ is the wavenumber. Note that this PSF is formulated for the case in which the same weights $w_{1,j}=w_{2,j}=w_j$ are used to compute $q_1(x, t)$ and $q_2(x, t)$ in (4). This equation can be simplified to find the spatial resolution for both the transverse and axial imaging planes by assuming w to be a smooth function. This allows us to write the PSF as $$P(x,f) = |\int_{-\infty}^{\infty} w(l) \exp\{j\Phi(x_{j_l})\} dl|^2 \quad (13)$$

Figure 3:
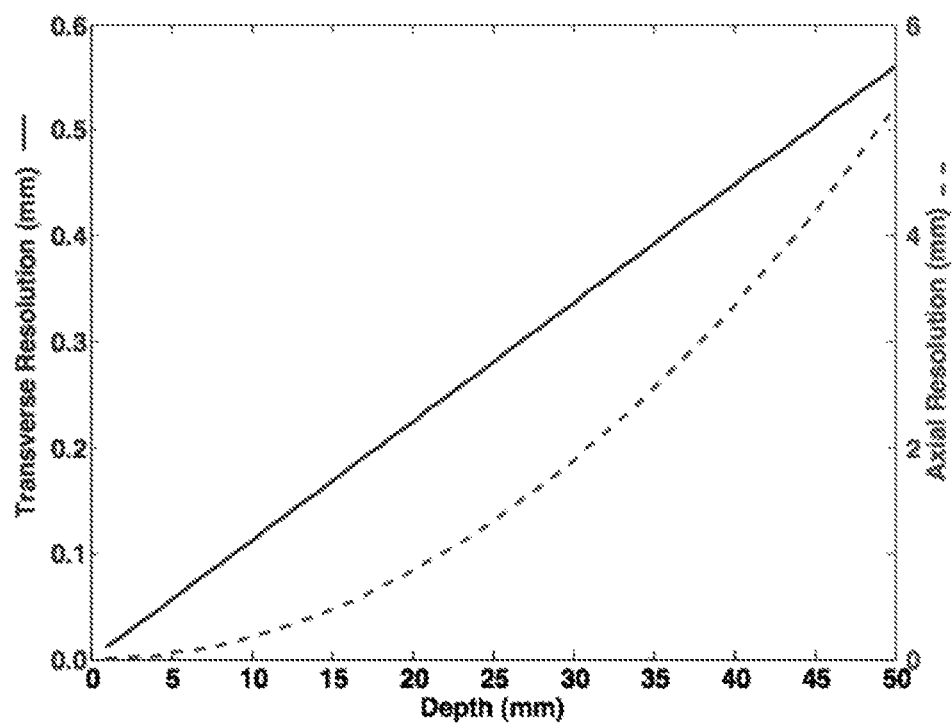
FIG. 3 is a graph of axial and transverse resolution as a function of depth for an array forming part of an embodiment of the invention.

For the transverse plane, $z=z_s$ and letting $\delta x = x-x_s$ and $\delta y = y-y_s$, the PSF can be shown to be $$P(x, f) = \left| \int_{-\infty}^{\infty} w(l) \exp\left\{ jk \frac{(\delta x + \delta y)}{z_s} \right\} dl \right|^2 \quad (14)$$

which is the Fourier transform of the aperture weighting function with scaled frequency $(k(\delta x + \delta y))/z_s$. For uniform weighting, and ignoring grating lobes, this would simply be the square of the sine function, or $$P(\delta x, \delta y, f) = \text{sinc}\left( \frac{Lk\sqrt{\delta x^2 + \delta y^2}}{2\pi z_s} \right)^2 \quad (15)$$

where $L=\sqrt{L_x^2+L_y^2}$ is the aperture size. Similarly, to find the axial resolution, assume a smooth, uniform weighting function and axisymmetry (an approximation for noncircular arrays), the Fresnel integral allows us to represent the PSF as $$P(\delta z, f) = \frac{\left| F\left( \sqrt{\frac{k\delta z}{4\pi(z_s L)^2}} \right) \right|}{\sqrt{\frac{k\delta z}{4\pi(z_s L)^2}}} \quad (16)$$

where $F(\bullet)$ is the Fresnel integral. Plotting both the axial and transverse PSF versus depth (zs) allows the determination of the resolutions in both planes from the fullwidth at half-maximum value (FWHM) of the PSF peak. FIG. 3 shows the resolutions of the array versus depth for an array with a center frequency of f=3.75 MHz and a speed of propagation of 1500 m/s.

Sensor Array

Figure 4B:
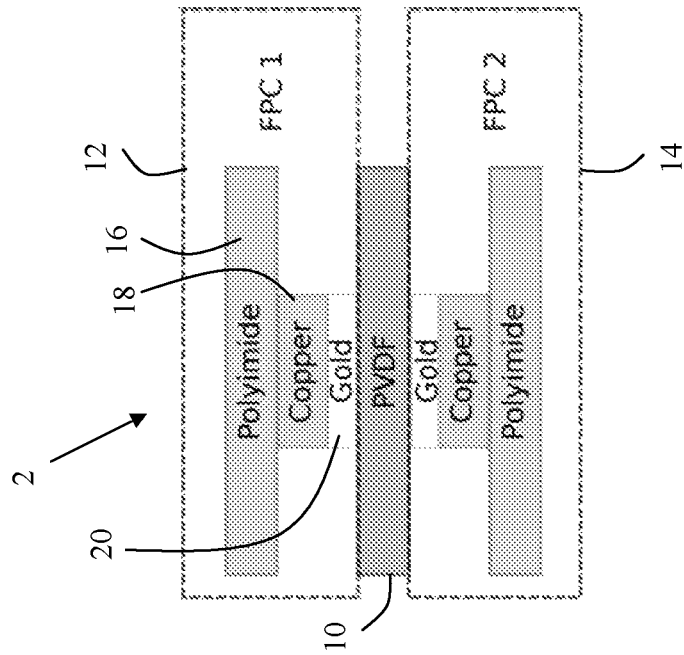
FIGS. 4a and 4b are schematic top and side views of a sensor array forming part of a further embodiment of the invention.
Figure 4A:
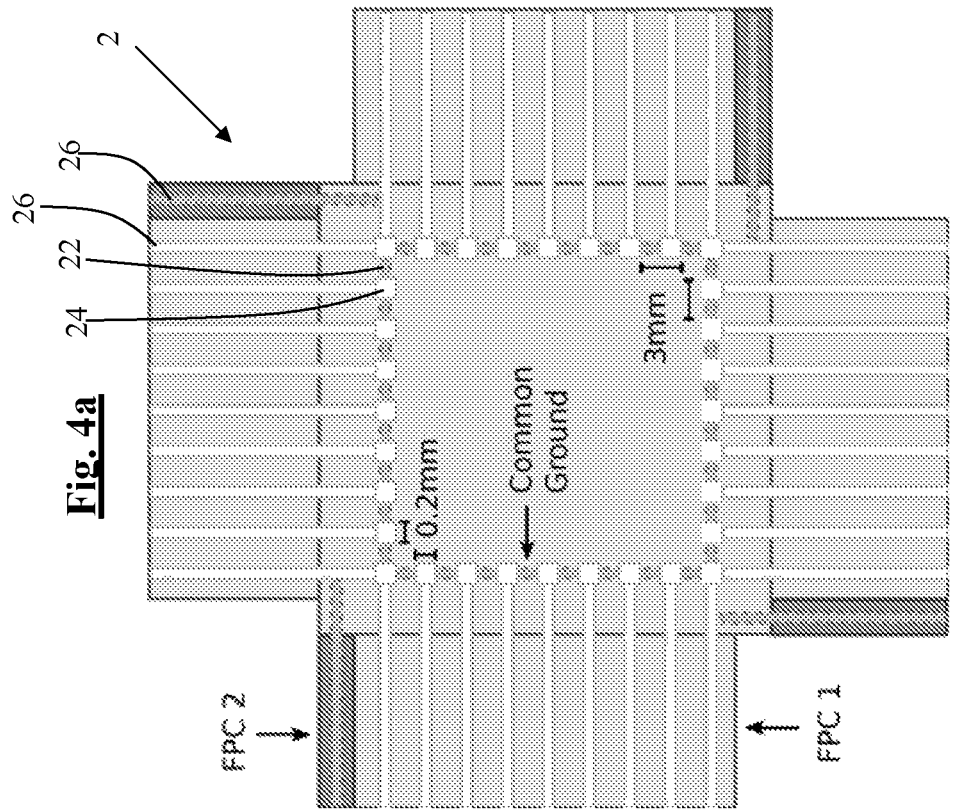

PVDF and its copolymers have been used in many applications involving acoustic sensors because of their low acoustic impedance, large receive bandwidth, and the material flexibility that facilitates custom nonrigid sensors. In fact, many of the widely reported uses for PVDF and P(VDF-TrFE) are in hydrophones, both single-element (needles and membranes) and arrays. Because the acoustic emissions in ultrasound therapy tend to have both harmonic and broadband components, a material with a large bandwidth and high receive efficiency is highly desired. Further, the relative cost in construction of an array made from prepoled PVDF film can be much less than conventional piezoceramic materials, such as PZT, because of the high manufacturing cost in dicing, wirebonding, and associated backing and matching layers. Referring to FIGS. 4a and 4b, the design of the 2-D PVDF array 2 created by Precision Acoustics (Dorchester, UK) will now be described. Prepoled 52-μm PVDF film 10 is layered between two custom flexible printed circuits (FPCs) 12, 12. Low-viscosity epoxy is used to bond the layers of the laminate together. Each FPC 12, 14 comprises a base layer 16 of polyimide, adhesivelessly bonded copper electrodes 18 and a final outer, oxidization resistant gold layer 20. Sensor elements are formed at the overlap region between electrodes on the two FPCs 12, 12. One FPC 12 acts solely as ground electrode and has a single electrode strip 22 (0.2 mm wide) that runs around the rectangular periphery of the array. This is shown in broken lines in FIG. 4a as it is on the FPC at the back as seen in FIG. 4a. The other FPC 14 has 32 electrodes 24 arranged to intersect the ground electrode perpendicularly such that the element count on any one side is N=9. Each of these signal-side electrodes is also of 0.2 mm width, and is on a center-to-center pitch of 3 mm. This arrangement yields a sparse rectangular boundary array with a final aperture size of 24.2×24.2 mm and active elements that are 0.2×0.2 mm.

The electrode connections 26 from each edge of the array are led out to a connection tab on the FPC that is designed for insertion into an industry-standard zero insertion force (ZIF) connector.

Experimental Setup

Two separate experiments were run to test the imaging quality of the sparse boundary array. First, a scattering experiment was run to determine the experimental PSF and compare it to the theoretical resolutions obtained previously. Second, the array was tested using a tissue-mimicking material (TMM) loaded with cavitation-nucleating particles to determine the passive acoustic mapping performance versus predictions.

Figure 5B:
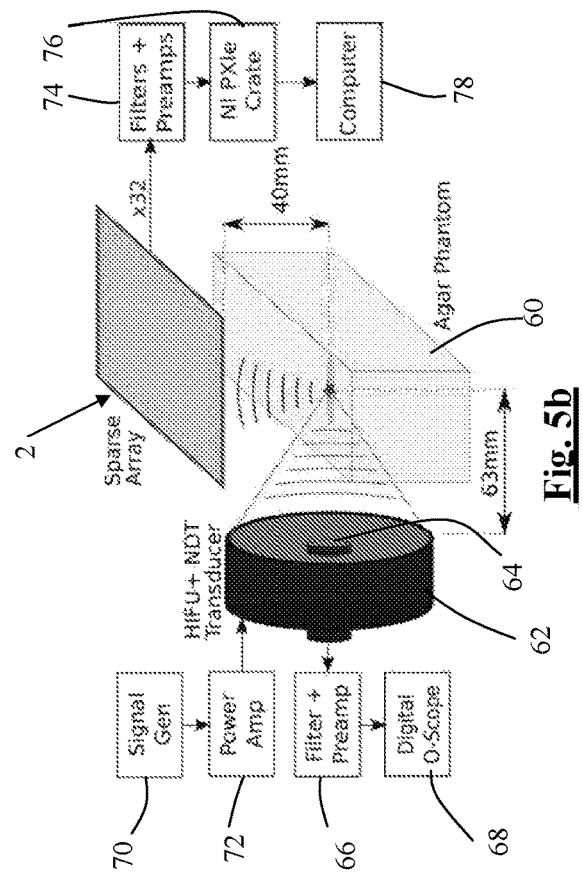
FIGS. 5a and 5b are diagrams of systems according to embodiments of the invention used to demonstrate the effectiveness of the invention.
Figure 5A:
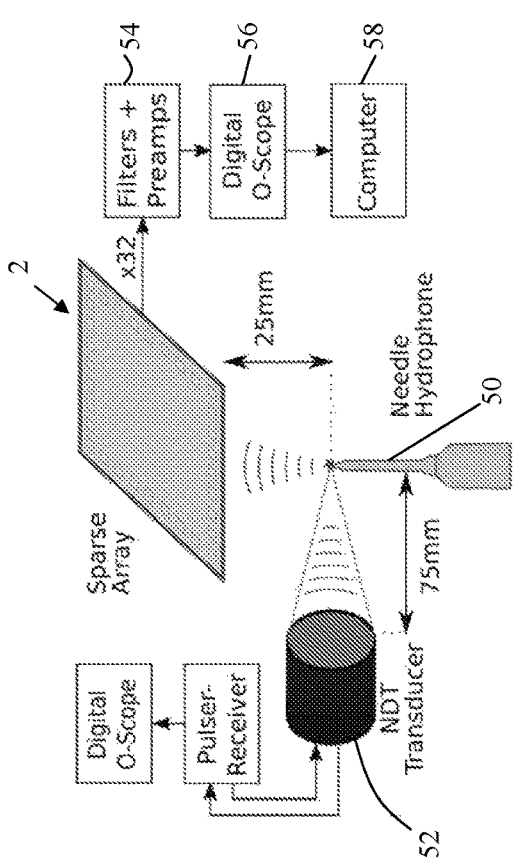

Referring to FIG. 5a in the scattering experiment, the tip of a 75-μm Precision Acoustics needle hydrophone 50 is used as a scattering point source, placed in the focus of an Olympus Panametrics (Waltham, Mass.) non-destructive testing (NDT) transducer 52 [0.5 in (12.7 mm) diameter, $f_o$=15 MHz]. The NDT transducer 52 has a focus of 75 mm, and the needle hydrophone 50 is arranged so that just the tip enters into the sound field. The (N=9) 32-element sparse rectangular boundary array 2 is arranged at 90° to the NDT transducer 52 and centered directly above the needle 50, as shown in FIG. 5(a). The source applied to the NDT transducer 2 was a broadband pulse from a DPR300 pulser-receiver (JSR Ultrasonics, Pittsford, N.Y.). The distance from the needle 50 to the sparse array 2 was determined experimentally to be approximately 25 mm so that all elements of the array were seeing the (weak) scattered signal from the needle tip. The signals collected by the array 2 were first sent to custom filters and preamplifier units 54 designed by Det Norske Veritas (Portland, UK). The high-pass filters have a cutoff of 1.5 MHz, and the preamplifiers are fixed gain of 37×. In the case of scattering, the array data was collected using a 44XI digital oscilloscope 56 (LeCroy Corp., Chestnut Ridge, N.Y.) averaging over 1000 pulses at $f_s$=250 MHz and transferred to PC for use with Matlab (The MathWorks Inc., Natick, Mass.). In all experiments, a 2-D raised cosine was used as the coarray weighting function, and the number of subimages was chosen based on a threshold of 95% of the total energy of the singular values.

Referring to FIG. 5b, for mapping cavitation, a homogeneous 3% aqueous agar gel as a TMM was prepared using deionized water. The agar is mixed with talc, a rough hydrophobic particle, which is used to provide consistent and repeatable cavitation results. For the mixture, 4.34 g of particles were added per 275 mL of 3% agar solution, and the mixture was degassed at −0.5 bar before pouring in a cast acrylic holder 60 with removable sides. Although the viscoelasticity of the TMM will make its cavitation behavior similar to that of tissue, its attenuation and speed of propagation will be quite similar to water. A 500-kHz HIFU transducer 62 (H-107-013, Sonic Concepts, Bothell, Wash.), confocally aligned axially with an Olympus Panametrics NDT transducer 64 [0.5 in (12.7 mm) diameter, fo=5 MHz, dfocus=75 mm], was used to initiate cavitation in the TMM. The NDT transducer 64 is used as a passive cavitation detector (PCD) to ensure the presence of cavitation and is connected first to a 2-MHz passive filter (Allen Avionics, Mineola, N.Y.), a 10× pre-amplifier 66 (Stanford Research Systems, Sunnyvale, Calif.), and the digital oscilloscope 68. The HIFU transducer 62 is driven with a function generator 70 (33250A, Agilent Technologies Inc., Santa Clara, Calif.) connected to a 55-dB power amplifier 72 (Model A300, Electronic Navigation Industries, Rochester, N.Y.) sending out a single 10-cycle sine wave at 500 kHz. It should be noted that the resulting cavitation maps were generated using only one 10-cycle pulse per map. As was done in the previous setup, the sparse rectangular boundary array 2 is aligned at 90° to the agar phantom, centered on the HIFU transducer focus. Finally, the signals from the array 2 are sent through the custom filters and preamplifiers 74 and then sampled by a National Instruments (Austin, Tex.) PXI Express (PXIe)-based data collection system 76. The system 76, which is eminently scalable and capable of on-board processing, consists of a field-programmable gate array (FPGA) card (NI PXIe-7962R) and adapter module (NI PXIe-5752) housed in a PXIe crate (NI PXIe-1082). A total of thirty-two 12-bit channels can be simultaneously sampled at 50 MHz. The data files are written directly to a PC 78 for processing with custom software written in Matlab.

Results

Figure 6:
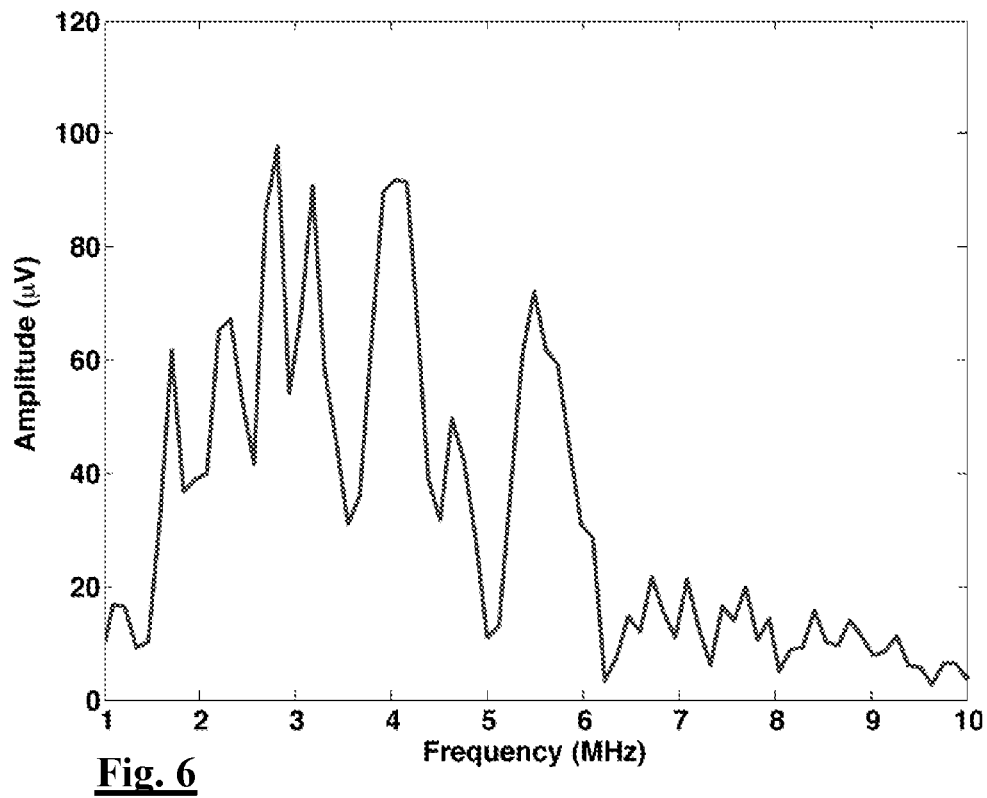
Figure 7B:
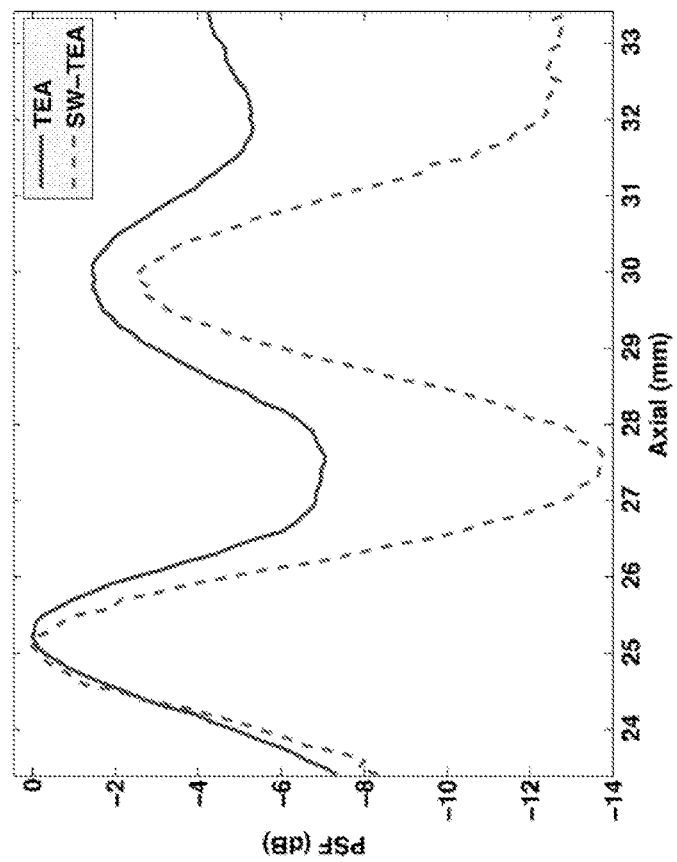
FIGS. 7a and 7b are transverse and axial point spread functions for the system of FIG. 5a using a known time exposure acoustics (TEA) algorithm and an algorithm according to the invention.
Figure 7A:
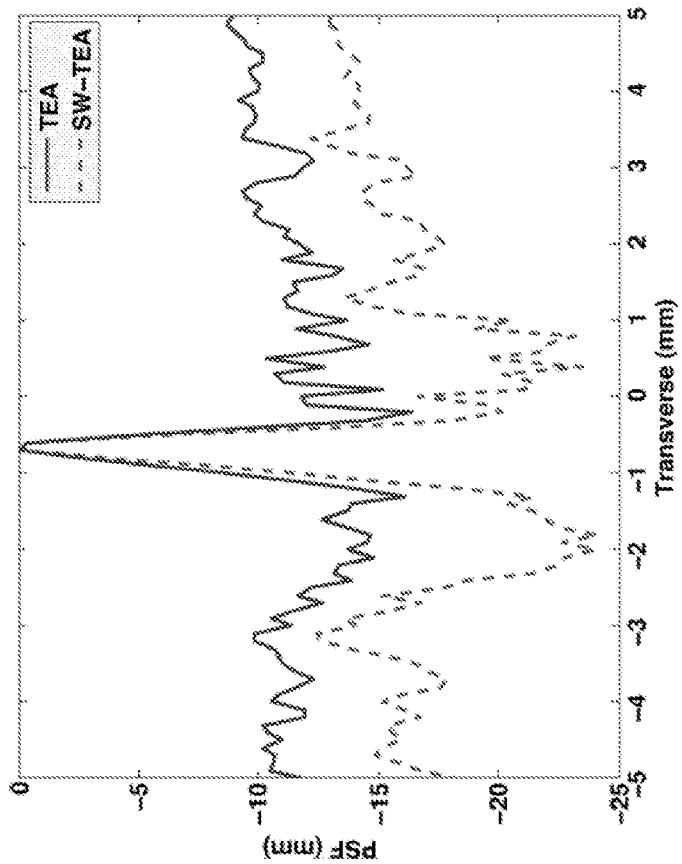

To determine the experimental PSF, the sparse rectangular boundary array recorded the scattered signals from the needle hydrophone with record length of 35 μs. The received bandwidth of the pulse at the array is approximately 3.75 MHz as shown in see FIG. 6. Thus, using the plot in FIG. 3, the expected resolution should be 0.28 mm transverse and 1.31 mm axially at 25 mm. The data were processed into passive acoustic maps using a conventional technique, time exposure acoustics (TEA) as described in [2]M. Gyongy, "Passive cavitation mapping for monitoring ultrasound therapy," Ph.D. dissertation, University of Oxford, Oxford, UK, 2011, as well as the sparse aperture weighted algorithm of Appendix 1 (here called SW-TEA) in Algorithm 1. The 1-D slices through the peaks are shown in FIGS. 7(a) and 7(b). The resolution in either plane will be represented by the FWHM value or the width of the peaks at the −6-dB points. For the transverse resolution, the TEA algorithm has a FWHM of 0.44 mm, and SW-TEA achieves a resolution of 0.34 mm. Similarly for the axial plane, the TEA algorithm has a resolution of 2.95 mm, and SW-TEA is again lower at 2.2 mm. In both cases, neither algorithm achieves exactly the theoretical resolution, but SW-TEA comes closest. That the theoretical resolution is not exactly achieved is not surprising: the SNR is very low because the point source is so small and is thus a weak scatterer. It is also not surprising that the SW-TEA performs better than standard TEA because the weighting function tends to reduce noise coming in through the side lobes. The double-peak in the axial plane can be explained by movement of the needle hydrophone resulting from acoustic pulse, thus giving two scattering points in the axial dimension in range. This also potentially explains why the transverse resolution is not exactly achieved, also because of needle movement.

Figure 8:
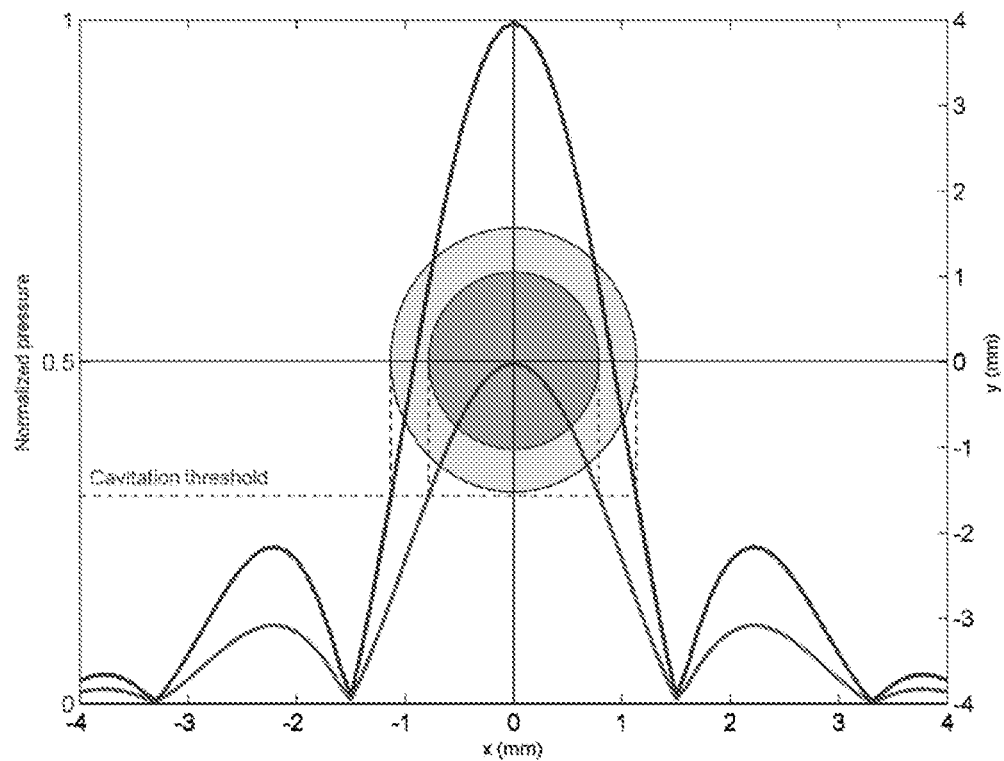
FIG. 8 is a diagram showing the extent of predicted cavitation produced in the system of FIG. 5b.
Figures 9A, 9B, 9C:
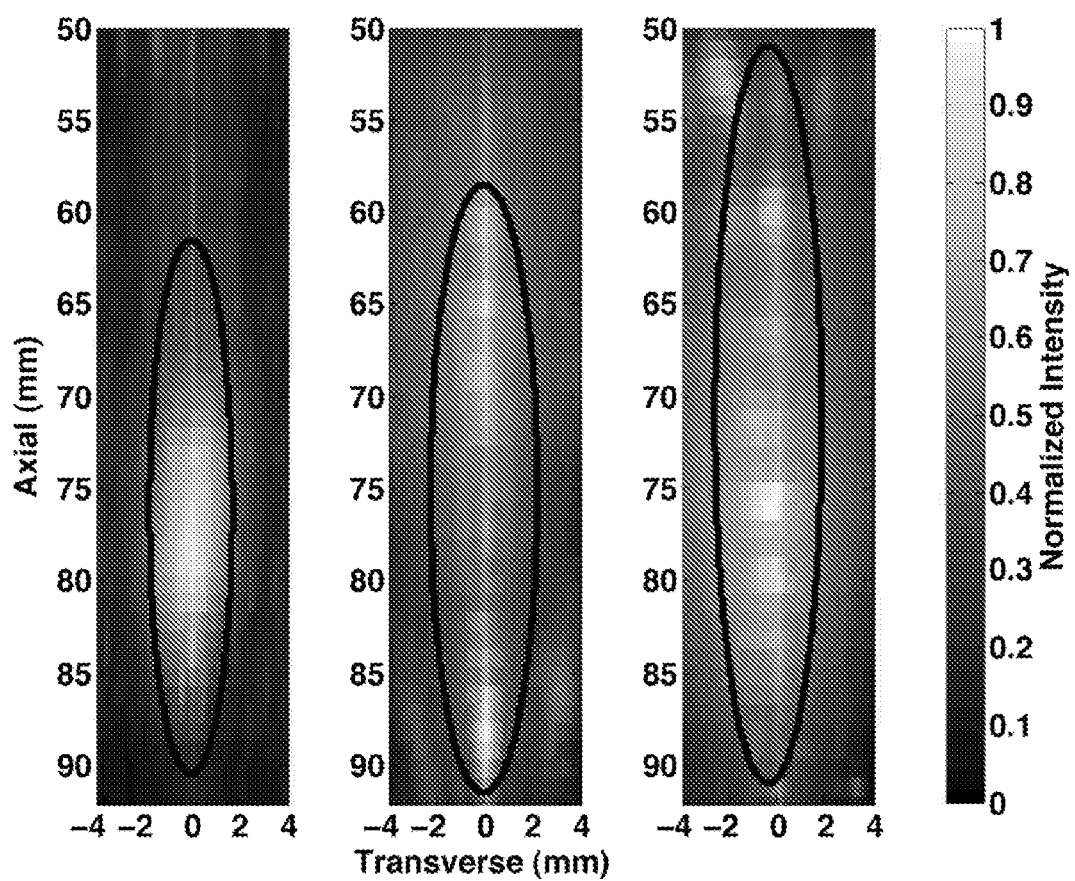
FIGS. 9a, 9b and 9c are images of cavitation produced in the system of FIG. 5b with different values of peak negative focal pressure.

One difficulty in assessing the accuracy of passive acoustic maps is the lack of alternative validated experimental techniques that enable accurate sizing of regions of inertial cavitation activity. It is possible, however, to predict the size of the region using knowledge of the cavitation threshold for the material and the transducer calibration. The cavitation threshold of this type of TMM has been found to be 1.42 MPa. Using an accurate calibration of the HIFU transducer, the predicted cavitation region should coincide with the size of the HIFU beam above the cavitation threshold at a particular insonating amplitude, as shown in FIG. 8. After data was collected using the setup in FIG. 5(b), the SW-TEA algorithm of Appendix 1 was used to generate cavitation maps. In FIG. 9, the resulting maps are shown for increasing peak negative focal pressures (PPNFP) of 2.23, 2.62, and 3.35 MMPa in the transverse-axial plane. In these images, the HIFU is travelling from top to bottom, thus the axial dimension is away from the HIFU transducer. The maps are also overlaid with black ellipses that represent the predicted inertial cavitation region for that insonating amplitude. From the images, it can be noted that the predicted inertial cavitation region correlates strongly with the experimental passive acoustic maps. As passive acoustic mapping has been previously shown to be able to discern discrete regions of cavitation activity, the double maxima in the 2.62 MPa exposure, while not an artifact of the algorithm, could be a result of uneven distribution of talc particles in the TMM, although too much should not be read into this. The main point is that the extent of activity corresponds closely to predicted size. It should also be noted that with TEA alone, maps showing cavitation regions were uninterpretable because of low SNR (mainly because of the small element sizes on the PVDF array) and side lobe noise. Thus, the use of the sparse array coupled with the ability to generate an array weighting by using the difference coarray with image addition also allows for improved passive acoustic mapping.

While the examples above relate to monitoring cavitation using broadband detection, the invention is also applicable to the monitoring of other effects, such as the mapping of harmonic emissions which can arise in a HIFU field from the scattering of the incident non-linear wave by tissue that lies within the focal volume.

---

Appendix Algorithm 1 Sparse Aperture Weighted Passive Beamforming.

---

Given: i indexes the pixels, j index sensor positions, x = (x, y, z)T, sj(t) is received sensor data for sensor j.
for i = 1 → $M_{pixels}$ do
Compute delay: $\{\tau_{ij} = d_{ij}/c : \forall_j\}$
Presteer data:
for j = 1 : 4(N − 1) do
$s_j(t) \leftarrow s_j(t + \tau_{ij})$
end for
Shift weight mask: C = γ(y) ← γ (y + $x_i$)
Map Weights: $C_w \leftarrow$ Transform{C}
Compute SVD: USVH C ← SVD($C_w$)
Threshold: $N_{subimage} \leftarrow$ threshold(S)
for l = 1 : $N_{subimage}$ do
Form Weights:
$w_1(l) \leftarrow u^l \sigma_1^{1/2}$
$w_1(l) \leftarrow v^l \sigma_1^{1/2}$
Apply weights:
$q_1(t; l) \leftarrow \beta \Sigma_{j=1}^{4(N-1)} w_{1,j}(l) d_{ij} s_j(t)$
$q_1(t; l) \leftarrow \beta \Sigma_{j=1}^{4(N-1)} w_{2,j}(l) d_{ij} s_j(t)$
Compute pixel values:

$$\Psi_{l,i} \leftarrow \frac{1}{4\pi\rho_0 cT} \int_{t_0}^{t_0+T} q_{1,i}(t; l) q_{2,i}(t; l)^* dt$$

end for
Sum subimages:

$$\Psi_{TOTAL,i} \leftarrow \sum_l \Psi_{l,i}$$

end for

---

The invention claimed is:

1. A passive imaging system for compression wave imaging, said imaging system arranged to generate an image by passive imaging, said image having a set of pixels, the system comprising an array of sensor elements arranged in a sparse array and each arranged to produce an output, and a processor arranged to:
store a plurality of samples of the output from each of the sensor elements over a sample period;
derive from the stored pluralities of samples a value for each of the set of pixels; wherein for each of the set of pixels the processor is configured to:
a. define a plurality of different sets of weights for the sensor elements of the sparse array;
b. calculate a component of a pixel value from each of the sets of weights and the stored pluralities of samples; and
c. sum the components of the pixel value to produce a final pixel value,
wherein the sparse array has a coarray, and, for each of the set of pixels, the weights are defined by a weight mask defined over the coarray, the weight mask has a centre, and the processor is configured
to position the weight mask such that during calculation of the components of the pixel value of one of the set of pixels, the centre of the weight mask is at a point in the coarray, and
to shift the weight mask such that during calculation of the components of the pixel value of each of the other pixels of the set of pixels, the centre of the weight mask is at a different respective point in the coarray.

2. An imaging system according to claim 1 wherein each of the set of pixels is arranged to represent a point, and for each of the set of pixels the processor is configured to calculate, for each of the sensor elements, a delay corresponding to a time the compression waves will take to travel from the point represented by the pixel to the sensor element.

3. An imaging system according to claim 2 wherein the processor is configured, for each of the set of pixels, to shift the stored plurality of samples from at least one of the sensor elements on the basis of the delays.

4. An imaging system according to claim 1 wherein for each of the set of pixels, the weights are related to each other by a weight mask function, and the weight mask function has a centre which is located at a different respective point in the coarray for each of the set of pixels.

5. An imaging system according to claim 4 wherein the weight mask function has a main area that corresponds to an area of the coarray, and a boundary area covering parts of the coarray not covered by the main area, the boundary area being of a single constant value.

6. An imaging system according to claim 1 wherein the processor is configured, in determining each of the sets of weights, to determine from the coarray weight mask an element space matrix having matrix elements corresponding to pairs of the array elements.

7. An imaging system according to claim 6 wherein the processor is configured to derive, from the element space matrix, at least one pair of weight vectors each having a weight for each of the array elements, and to derive from the pair of weight vectors a value for the pixel of the image.

8. An imaging system according to claim 7 wherein the processor is configured to derive, from the element space matrix, a plurality of pairs of weight vectors.

9. An imaging system according to claim 8 wherein the processor is configured to select from said plurality of pairs of weight vectors, a group of the most significant pairs, and to derive a pixel value only from each of said group.

10. A method of passive compression wave imaging, wherein said imaging produces a compression wave image comprising a set of pixels, the method comprising:
providing an array of sensor elements arranged in a sparse array and each arranged to produce an output;
storing a plurality of samples of the output from each of the sensor elements over a sample period;
deriving from the stored pluralities of samples a value for each of the set of image pixels;

wherein for each of the set of image pixels the method includes:

defining a plurality of different sets of weights for the sensor elements of the sparse array;

calculating a component of a pixel value from each of the sets of weights and the stored pluralities of samples; and summing the components of the pixel value to produce a final pixel value, wherein the sparse array has a coarray, and for each of the set of pixels, the weights are related to each other by a weight mask defined over the coarray, wherein the weight mask has a centre, and is positioned such that, during calculation of the components of the pixel value of one of the set of pixels, the centre of the weight mask is at a point in the coarray, and the weight mask is shifted such that during calculation of the components of the pixel value of each of the other pixels of the set of pixels, the centre of the weight mask is at a different respective point in the coarray.

11. A method according to claim 10 wherein each of the set of pixels is arranged to represent a point, the method including, for each of the set of image pixels, calculating for each of the sensor elements, a delay corresponding to the time the compression waves will take to travel from the point represented by the pixel to the sensor element.

12. A method according to claim 11 including, for each of the set of pixels, shifting the stored plurality of samples from at least one of the sensor elements on the basis of the delays.

13. A method according to claim 10 including, for each of the set of pixels, deriving the weights using a weight mask function, and shifting the weight mask function for each of the set of pixels.

14. A method according to claim 13 wherein the weight mask function has a main area that corresponds to the area of the coarray, the method including, identifying elements of the coarray not covered by the main area of the weight mask function and allocating a single constant value to those points.

15. A method according to claim 14 wherein determining each set of weights includes determining from the coarray weight mask an element space matrix having matrix elements corresponding to pairs of the array elements.

16. A method according to claim 15 including deriving, from the element space matrix, at least one pair of weight vectors each having a weight for each of the array elements, and deriving from the pair of weight vectors a value for the pixel of the image.

17. A method according to claim 16 including deriving from the element space matrix, a plurality of pairs of weight vectors.

18. A method according to claim 17 including selecting from said plurality of pairs of weight vectors, a group of the most significant pairs, and deriving a pixel value only from each of said group.

* * * * *